United States Patent
Fukaya et al.

[11] Patent Number: 5,874,663
[45] Date of Patent: Feb. 23, 1999

[54] WATERPROOF STRUCTURE FOR AN AIR-FUEL RATIO SENSOR

[75] Inventors: Kenji Fukaya, Chiryu; Makoto Hori, Oogaki; Masahiro Hamaya, Anjo; Masatoshi Suzuki, Nagoya, all of Japan

[73] Assignee: Denso Corporation, Kariya, Japan

[21] Appl. No.: 786,035

[22] Filed: Jan. 21, 1997

[30] Foreign Application Priority Data

Jan. 18, 1996 [JP] Japan .................................. 8-006819

[51] Int. Cl.$^6$ .............................................. G01N 27/409
[52] U.S. Cl. ..................................... 73/23.32; 123/688
[58] Field of Search .............................. 73/23.31, 23.32, 73/118.1, 118.2; 364/431.051, 431.062; 123/688

[56] References Cited

U.S. PATENT DOCUMENTS

| | | | |
|---|---|---|---|
| 4,308,518 | 12/1981 | Hattori et al. | 73/23.31 |
| 4,442,420 | 4/1984 | Novak | 338/34 |
| 4,443,781 | 4/1984 | Ohta et al. | 73/23.31 |
| 4,596,132 | 6/1986 | Takami et al. | 73/23.31 |
| 5,089,133 | 2/1992 | Kato et al. | 204/427 |
| 5,329,806 | 7/1994 | McClanahan et al. | 73/31.05 |
| 5,467,636 | 11/1995 | Thompson et al. | 73/23.31 |
| 5,490,412 | 2/1996 | Duce et al. | 73/23.31 |
| 5,602,325 | 2/1997 | McClanahan et al. | 73/23.31 |
| 5,616,825 | 4/1997 | Achey et al. | 73/23.31 |

FOREIGN PATENT DOCUMENTS 5-087769   4/1993   Japan .

*Primary Examiner*—George M. Dombroske
*Attorney, Agent, or Firm*—Cushman Darby & Cushman IP Group of Pillsbury Madison & Sutro LLP

[57] ABSTRACT

An air-fuel ratio sensor is provided in which sensor lead wires are held by a rubber bush at an end of a sensor housing. The rubber bush is made of a rubber material having a 100% modulus strength equal to or larger than 60 Kgf/cm$^2$ even after the sensor is used under a temperature environment of 300° C. for 100 hours.

7 Claims, 3 Drawing Sheets

WATERPROOF STRUCTURE FOR AN AIR-FUEL RATIO SENSOR

BACKGROUND OF THE INVENTION

1. Field of the Invention

The present invention relates to an improvement of an air-fuel ratio sensor which is, for example, installed on an intake or exhaust gas pipe of an internal combustion engine for an automotive vehicle for detecting a ratio of fuel to air in the intake or exhaust gas, and more particularly to an improvement of a waterproof sealing structure applied to a portion where lead wires are fixed by a rubber bush and subjected to a high-temperature environment.

2. Related Art

Conventionally, air-fuel ratio sensors of automotive engines have been located fixedly at various positions in engine exhaust systems. Particularly, when an air-fuel ratio sensor is installed under a floor of a vehicle body, there is a possibility that the air-fuel ratio sensor is exposed to water. Thus, it is necessary to enhance the reliability of the waterproof structure for surely preventing water from entering into the sensor.

In general, any permeation of water into the sensor body causes an undesirable change of the oxygen concentration detected by the sensor. As apparent from the operating principle of the air-fuel ratio sensor, it is already known that such a change possibly results in a malfunction of the air-fuel ratio sensor.

A sealing rubber bush is used at a portion where lead wires are taken out from the sensor body. To improve the waterproof structure of an air-fuel ratio sensor, this kind of sealing rubber bush have -been usually made of a fluorine-contained rubber or silicone rubber having an excellent heat resistivity.

Recent change of automotive vehicle environments, such as enforcement of the latest European regulation on exhaust gas emission (i.e. reduction of harmful components involved in exhaust gas during a high-speed cruising condition), will increase the temperature of exhaust gas as a result of improvement of combustion efficiency in an engine. This will lead to severe deterioration or damage of a rubber bush of an air-fuel ratio sensor installed closely to an engine exhaust pipe in which high-temperature exhaust gas flows. For example, there is a possibility that the rubber bush is subjected to a high-temperature atmosphere of 300° C.

A problem is that a conventional fluorine-contained rubber bush or a silicone rubber bush is speedily decomposed or cracked under such a severe condition of 300° C., damaging the waterproof structure.

Furthermore, there is a tendency that an air-fuel ratio sensor is downsized to improve its installation onto an automotive vehicle. However, such a size reduction of an air-fuel ratio sensor may force the rubber bush to be subjected to a further severe (higher temperature) condition. Thus, the deterioration of the waterproof structure will be expedited.

SUMMARY OF THE INVENTION

Accordingly, in view of above-described problems encountered in the related art, a principal object of the present invention is to provide an improved waterproof structure for an air-fuel ratio sensor using a rubber bush subjected to high-temperature environments.

In order to accomplish this and other related objects, the present invention provide a novel and excellent air-fuel ratio sensor having various aspects described hereinafter with reference to numerals in parentheses which show the correspondence to the components of the preferred embodiments of the present invention described later.

To improve the reliability of the waterproof structure in a high-temperature atmosphere, inventors of this application have first found the following phenomenon through try and error in the process of studying various materials used for a rubber bush (33).

In general, many of engineers in this field have been focusing on the compressive strength of a rubber bush under a caulking operation. However, the inventors of this application have found the fact that a tensile strength plays an important role in causing a crack in a rubber bush rather than a thermal expansion coefficient difference between a rubber bush and a metallic cover. Thus, the inventors of this application have paid their attention upon an 100% modulus strength (i.e. a tensile strength obtained when a sample is extended double) of a rubber material. And, they have confirmed that the waterproof sealing ability of a rubber bush can be effectively improved by setting this 100% modulus strength to be equal to or larger than 60 $Kgf/cm^2$ after an elapse of 100 hours under a temperature environment of 300° C.

More specifically, the present invention provides an air-fuel ratio sensor comprising a sensor element (11) for detecting an air-fuel ratio of gas fluid to be sensed, housing members (10, 12, 13, 14) for holding and fixing the sensor element (11), lead wires (29, 30, 31) having one end connected to the sensor element (11), an intermediate portion extending inside the housing members (10, 12, 13, 14), and the other end taken out from an opening provided at an end portion of the housing members (10, 12, 13, 14); and a rubber bush (33) disposed inside the end portion of the housing members (10, 12, 13, 14) and having through holes into which the lead wires (29, 30, 31) are inserted. Furthermore, a compressive stress is given to the rubber bush (33) disposed inside an end portion of housing members (10, 12, 13, 14) by these housing members to hermetically fix lead wires (29, 30, 31) of the sensor element (11) detecting an air-fuel ratio of gas fluid to be sensed. And, the rubber bush (33) is made of a rubber material having an 100% modulus strength (i.e. a tensile strength obtained when a sample is extended double) equal to or larger than 60 $Kgf/cm^2$ after an elapse of 100 hours under a temperature environment of 300° C.

With this arrangement, as shown in FIG. 2 later explained, both of a crack generation in rubber bush (33) and a gas leak amount can be reduced. Thus, the waterproof sealing ability of a rubber bush can be effectively improved.

Furthermore, according to features of preferred embodiments of the present invention, the rubber bush (33) is caulked by an end portion of housing members (10, 12, 13, 14) at a caulking rate of 10 to 35%. By setting the caulking rate in this range, it becomes possible to surely prevent the rubber bush (33) from causing cracks and maintain an excellent waterproof sealing ability for a long time.

Furthermore, it is preferable that a multiple caulking structure comprising at least two caulking portions is provided on the opened end portion of housing members (10, 12, 13, 14). This multiple caulking structure is effective to increase the number of caulking seal portions, and effective to increase a contact area between rubber bush (33) and lead wires (29, 30, 31). Thus, there is a merit of surely fixing lead wires (29, 30, 31) with rubber bush (33). At the same time, a sealing area at the caulking seal portion can be increased.

This is advantageous in that the waterproof sealing ability is further improved.

Moreover, adopting the above-described multiple caulking structure is advantageous in that the waterproof sealing structure can be adequately maintained because of an increase of sealing area capable of compensating a reduction of caulking rate of rubber bush (33). Reduction of the caulking rate leads to a reduction of a compressive permanent distortion due to heat and aging of rubber bush (33). Thus, the durability of rubber bush (33) can be improved.

Still further, it is preferable that part of rubber bush (33) located between two caulking portions (33b, 33c) is brought into hermetical contact with the inside wall of the housing member after the rubber bush (33) is deformed by the caulking operation. With this arrangement, the sealing ability can be effected by an axially extending region between two caulking portions (33b, 33c). Even if the sealing ability is reduced locally at these caulking portions (33b, 33c) due to the deterioration (compressive permanent distortion), the overall sealing ability of rubber bush (33) can be adequately maintained as long as rubber bush (33) is hermetically contacted with the inside wall of the housing member in the axially extending region between two caulking portions (33b, 33c).

BRIEF DESCRIPTION OF THE DRAWINGS

The above and other objects, features and advantages of the present invention will become more apparent from the following detailed description which is to be read in conjunction with the accompanying drawings, in which.

DETAILED DESCRIPTION OF THE PREFERRED EMBODIMENTS

Figure 1:
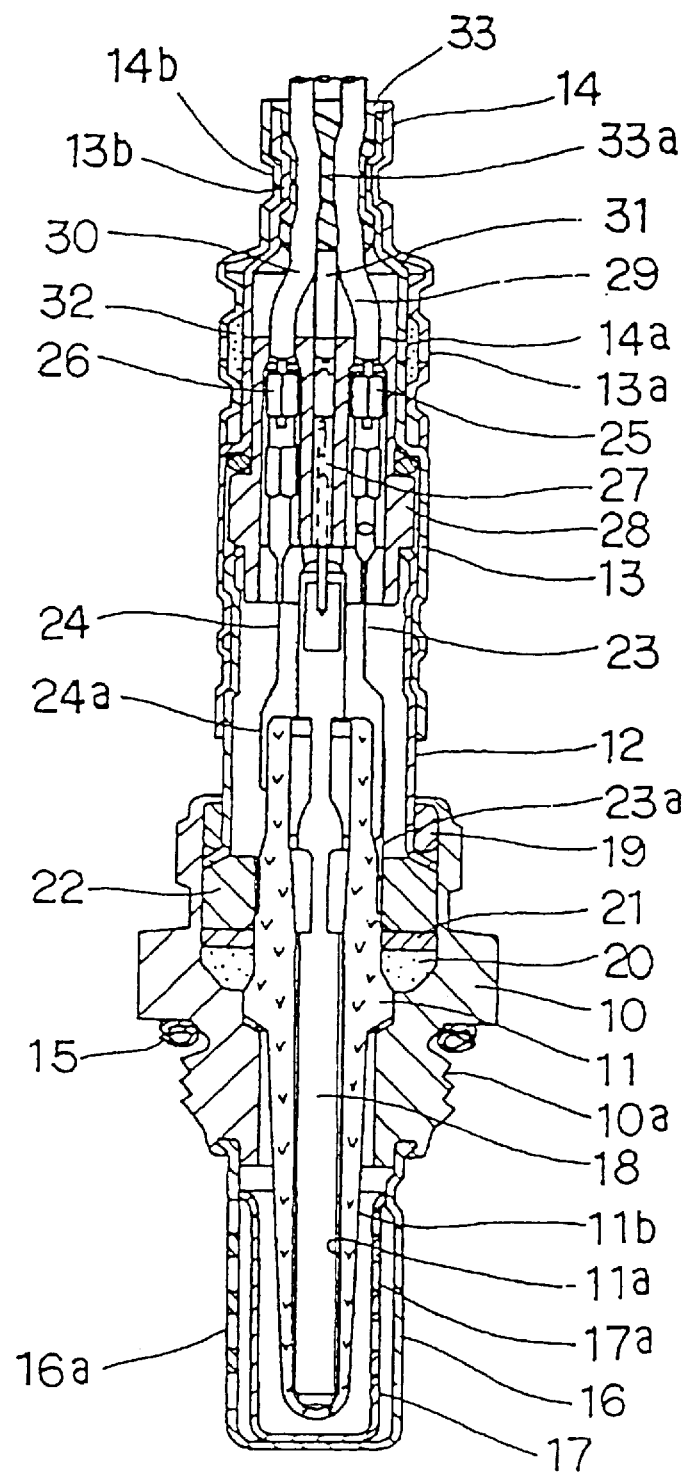
FIG. 1 is a vertical cross-sectional view showing an air-fuel ratio sensor in accordance with a first embodiment of the present invention.

Hereinafter, preferred embodiments of the present invention will be explained with reference to the accompanying drawings. Identical parts are denoted by the same reference numerals throughout views.

First Embodiment

An air-fuel ratio sensor of the first embodiment is installed on an exhaust gas pipe of an automotive vehicle engine to detect an air-fuel ratio of exhaust gas. As shown in FIG. 1, the air-fuel ratio sensor comprises a cylindrical housing 10, a sensor element 11 fixedly inserted in this housing 10, and cylindrical covers 12, 13, 14 disposed above the housing 10 to cover the upper side of sensor element 11.

Housing 10 and covers 12, 13 and 14, cooperatively serving as housing members of the air-fuel ratio sensor, are made of stainless metal excellent in corrosion and heat resistivity. Sensor element 11, which is a well-known type, is formed into a cup shape and made of a solid electrolyte such as zirconia ($ZrO_2$). An atmospheric chamber is formed at a central portion of this sensor element 11. This atmospheric chamber is communicated with the outside of the sensor body through a later-described passage. An inside (atmospheric air side) electrode 11a and an outside (exhaust gas side) electrode 11b are formed on inner and outer cylindrical surfaces of sensor element 11, respectively. These inside and outside electrodes 11a and 11b are made of noble metal such as platinum.

Operational principle of the sensor element 11 for detecting an air-fuel ratio is well-known and, therefore, will be explained simply hereinafter. The sensor element 11, as a concentration cell, generates an electromotive force corresponding to a difference between an oxygen concentration of the atmospheric chamber sensible through inside electrode 11a and an oxygen concentration of the exhaust gas sensible through outside electrode 11b. An air-fuel ratio of exhaust gas is thus detectable from the electromotive force.

Housing 10 has an installation screw portion 10a integrally formed on an outer cylindrical surface thereof. The air-fuel ratio sensor is hermetically fixed to an exhaust gas pipe (not shown) at this installation screw portion 10a by means of a gasket 15. Accordingly, the lower portion of sensor element 11 is inserted into the exhaust gas pipe. The outside (exhaust gas side) electrode 11b of sensor element 11 is exposed or subjected to exhaust gas introduced through small holes 16a and 17a opened on double cylindrical covers 16 and 17 installed on the housing 10.

Furthermore, an electric heater 18 is inserted into the central portion (i.e. atmospheric chamber) of sensor element 11. This electric heater 18 generates heat chiefly when the engine is operated in a low-temperature region, thereby warming up sensor element 11 sufficiently to operate in an ordinary fashion. The upper annular edge of housing 10 is integrally caulked with the lower annular edge of cover 12 through a metal ring 19. The caulking force, generated in the engagement of the annular edge of housing 10 and the lower annular edge of cover 12, is transmitted via a pad 21 and an insulator 22 to ceramic sealing powder 20. Thus, ceramic sealing powder 20 is pressed to a stepped portion of housing 10. With this arrangement, housing 10 and cover 12 are sealed at their connecting portions. A similar caulking structure is provided between covers 12 and 13 to integrally connect them, and between covers 13 and 14, too.

Minus and plus terminal pieces 23 and 24 are made of conductive spring metal. A lower end portion 23a of minus terminal piece 23 is elastically press-fitted on an outer cylindrical surface of an intermediate stepped portion of sensor element 11, and is electrically connected to the outside electrode 11b of sensor element 11. Meanwhile, a lower end portion 24a of plus terminal piece 24 is elastically press-fitted on an outer cylindrical surface of an upper smaller-diameter portion of sensor element 11.

The inside electrode 11a of sensor element 11 is elongated to the place where the lower end portion 24a of plus terminal piece 24 is press-fitted. Hence, the plus terminal piece 24 is electrically connected to the inside electrode 11a of sensor element 11.

The upper ends of terminal pieces 23 and 24 are electrically connected to connectors 25 and 26, respectively. Electric heater 18 is electrically connected to a connector 27. These connectors 25, 26 and 27 are inserted into through holes formed in a ceramic insulator 28. Furthermore, these connectors 25, 26 and 27 are electrically connected to lead wires 29, 30 and 31 for electrical connection to an external circuit.

In FIG. 1, connector 27 and lead wire 31 have the same polarity. The other couple of a connector and a lead wire having an opposite polarity is not shown in the drawing. Through holes 13a and 14a are opened on covers 13 and 14, respectively, at a coupled or lapped region thereof. A filter member 32 is disposed between these through holes 13a and 14a. Filter member 32 has a function of removing water or dust entering from the outside. In other words, the central portion (i.e. atmospheric chamber) of sensor element 11 is communicated with the outside through these through holes 13a, 14a and filter member 32.

The upper annular end of covers 13 and 14 are both opened. The lead wires 29, 30 and 31 are taken out from these opened ends of covers 13 and 14 to the outside. A rubber bush 33 is disposed inside the opened annular end region of united covers 13 and 14. The rubber bush 33 has through holes extending in the axial direction along which lead wires 29, 30 and 31 are inserting. Thus, lead wires 29, 30 and 31 are fixedly supported by rubber bush 33.

The support and fixing structure of lead wires 29, 30 and 31, realized by rubber bush 33, is essential for the present invention. Therefore, details of this support and fixing structure will be explained hereinafter.

Rubber bush 33 is formed into a cylindrical body having through holes extending in the axial direction for supporting lead wires 29, 30 and 31 therein. After the lead wires 29, 30 and 31 are inserted into these through holes, a caulking operation is performed to firmly fix the lead wires 29, 30 and 31 with rubber bush 33. More specifically, a caulking force acting in the radially inward direction is applied to a predetermined position 13b, 14b on the opened annular end region of the united covers 13 and 14. The axial position of these caulking position 13b, 14b just meets an axial center 33a of rubber bush 33. Through this caulking operation, the axial center 33a of rubber bush 33 is elastically pressed and deformed so as to form an annular groove. A compressive stress, thus generated, forces the axial center 33a of rubber bush 33 to press-fit to the lead wires 29, 30, 31 and the inside wall of cover 13, effecting a waterproof sealing ability.

However, the air-fuel ratio sensor of the present invention is installed on the exhaust pipe of an automotive engine. High temperature heat of exhaust gas is transferred or radiated to the opened annular end region of the united covers 13 and 14. Thus, there is a possibility that rubber bush 33 is subjected to high temperature of 300° C. As a result, rubber bush 33 receives adverse effects of high temperature and may cause an aging phenomenon, thus generating a crack or deteriorating a waterproof sealing function.

In view of the foregoing, to improve the reliability of the waterproof structure in a high-temperature atmosphere, the inventors of this application have paid their attention upon an 100% modulus strength (i.e. a tensile strength obtained when a sample is extended double) of a rubber material through try and error in the process of studying various materials used for a rubber bush 33. Numerous samples of rubber bush 33 were produced from materials having various modulus strengths. These samples were exposed to a 300° C. atmosphere for 100 hours. Then, both a crack generation rate and a gas leak amount of rubber bush 33 were measured to evaluate a relationship between these physical quantities and the 100% modulus strength. FIG. 2 shows the result of the crack generation rate and the gas leak amount thus measured.

For the tests of crack generation rate, experiments were conducted under two caulking rates of 10% (black round marks) and 35% (white round marks). With these two caulking rates, numerous materials for rubber bush 33 were tested under the same condition of 300° C. and 100 hours, to measure both of the crack generation rate and the gas (air) leak amount of rubber bush 33.

In general, the caulking rate is defined by the following equation 1, when "a" represents a thickness of rubber bush 33 in a free condition where a caulking operation is not yet performed and "b" represents a thickness of rubber bush 33 in a compressed and deformed condition where the caulking operation is already finished.

$$\text{caulking rate} = \{(a-b)/a\} \cdot 100(\%) \tag{1}$$

Furthermore, the crack generation rate is obtained from an observation for visually checking a percentage of crack-generating samples among all of tested samples.

Figure 2A:
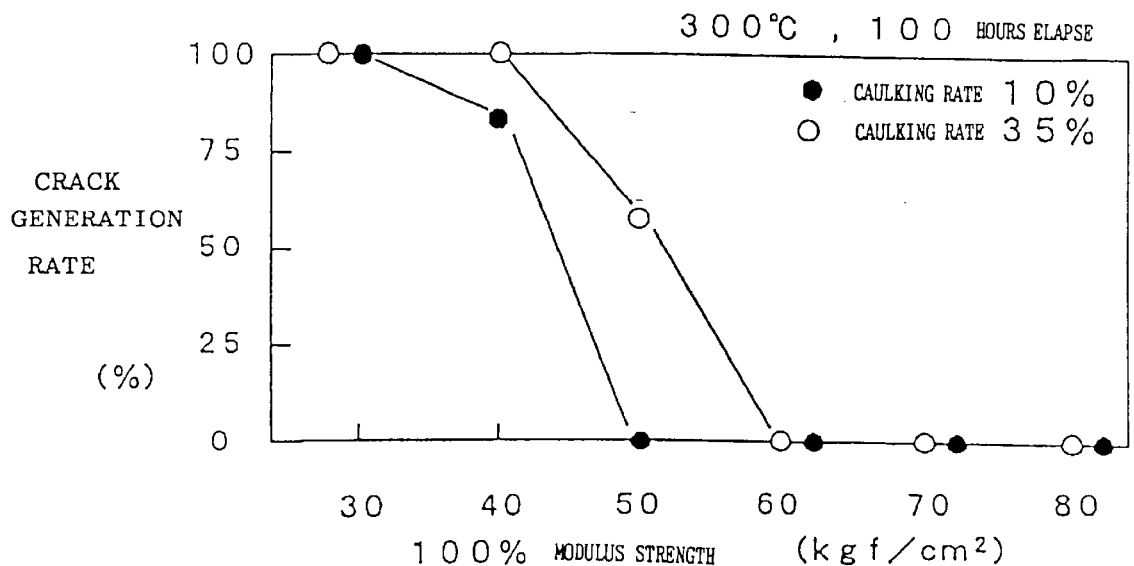
FIG. 2A is a graph showing a relationship between 100% modulus strength of a rubber bush and a crack generation rate in accordance with the present invention.

As understood from the experiment result of FIG. 2A, it is confirmed that the crack generation rate can be reduced to 0 when a rubber material has an 100% modulus strength equal to or larger than 60 Kgf/cm$^2$ after an elapse of 100 hours under a temperature environment of 300° C.

Figure 2B:
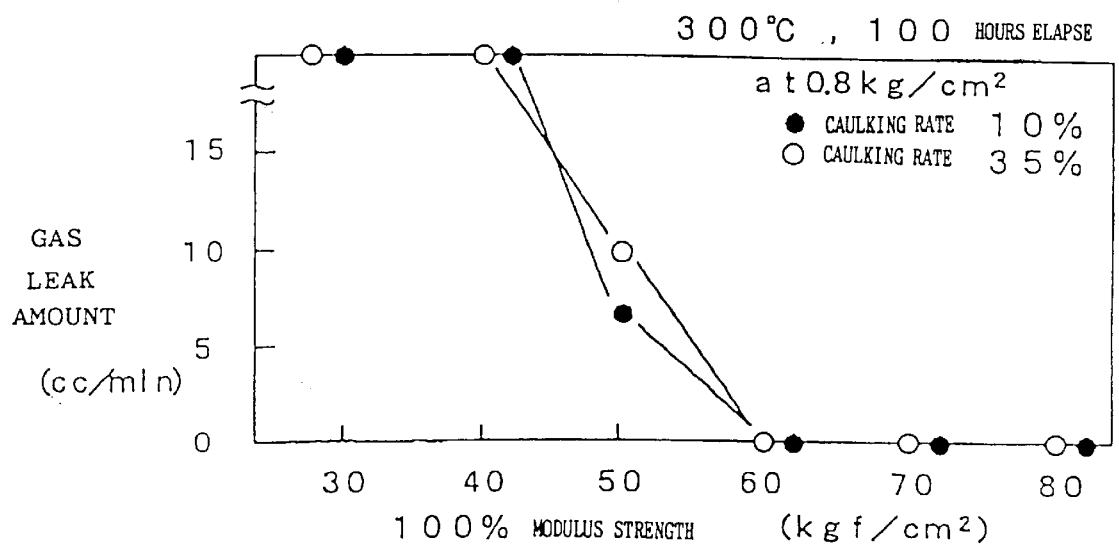
FIG. 2B is a graph showing a relationship between 100% modulus strength of a rubber bush and a gas leak amount in accordance with the present invention.

FIG. 2B shows a relationship between the gas leak amount of rubber bush 33 and the 100% modulus strength. For the tests of gas leak amount, experiments were conducted under the following conditions. In the experiments, housing 10 and cover 12 of FIG. 1 were disconnected to open the lower end of cover 12. From this opened lower end of cover 12, gas having a pressure of 0.8 Kg/cm$^2$ (gauge pressure) was introduced. The upper open end region of the united covers 13, 14 was submerged into water for one minute. Then, the gas amount leaking into water through rubber bush 33 was measure.

As understood from the experiment result of FIG. 2B, it is confirmed the gas leak amount can be reduced to 0 when a rubber material has an 100% modulus strength equal to or larger than 60 Kgf/cm$^2$ after an elapse of 100 hours under a temperature environment of 300° C.

In view of the foregoing results, it is concluded that the waterproof sealing ability of rubber bush 33 can be maintained adequately for a long time even under a severe environment of 300° C. as long as rubber bush 33 is made of a rubber material having an 100% modulus strength equal to or larger than 60 Kgf/cm$^2$ after an elapse of 100 hours under a temperature environment of 300° C. Material preferable for rubber bush 33 are, for example, tetrafluoroethylene-perfluoroether, tetrafluoroethylene-perfluoromethyl, vinyl, and ether.

Regarding the caulking condition of rubber bush 33, it is confirmed from the result of FIGS. 2A and 2B that the waterproof sealing ability can be nicely maintained when the caulking rate is in a range of 10 to 35%.

Second Embodiment

Figure 3:
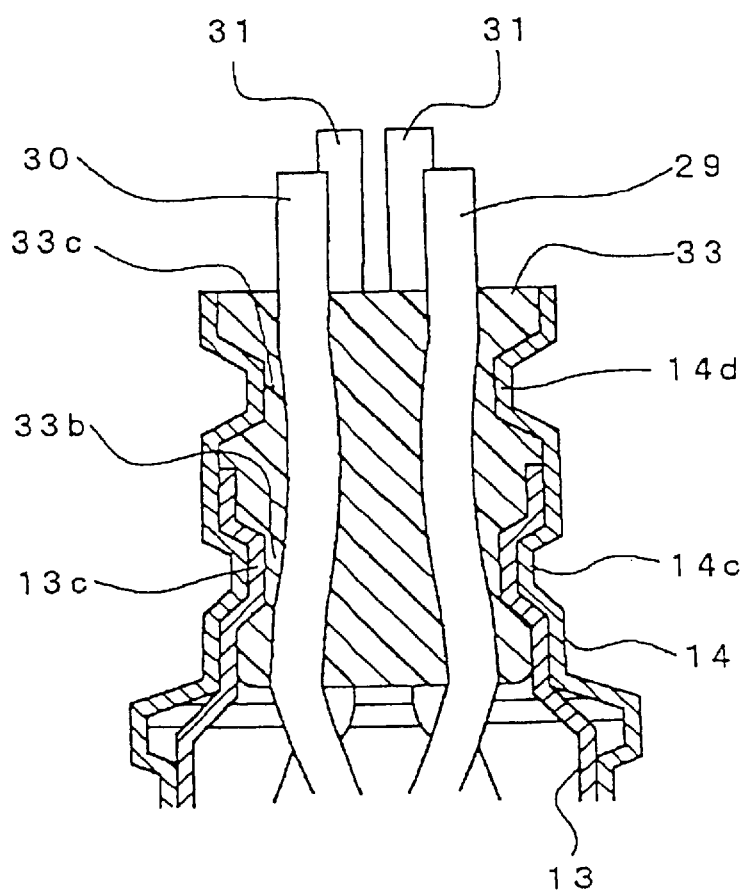
FIG. 3 is a vertical cross-sectional view showing part of an air-fuel ratio sensor in accordance with a second embodiment of the present invention.

FIG. 3 shows a second embodiment of the present invention which is characterized by a multiple caulking structure according to which rubber bush 33 is caulked at two portions 33b and 33c spaced in the axial direction. In FIG. 3, reference numerals 13c, 14c and 14d represent caulked portions (recessed portion) of covers 13 and 14.

Providing at least two caulked portions on rubber bush 33 in accordance with the second embodiment of the present invention is advantageous in that the number of caulking seal portions is increased and the contact area between rubber bush 33 and lead wires 29, 30 and 31 can be increased. Thus, this brings a merit in that lead wires 29, 30 and 31 can be surely fixed. At the same time, an increase of the seal area at the caulking seal portions is preferable in that the waterproof sealing ability can be further improved.

Moreover, adopting the above-described multiple caulking structure is advantageous in that the waterproof sealing structure can be adequately maintained because of an increase of sealing area capable of compensating a reduction of caulking rate of rubber bush 33. Reduction of the caulking rate leads to a reduction of a compressive permanent distortion due to heat and aging of rubber bush 33. Thus, the durability of rubber bush 33 can be improved.

Still further, it is preferable that part of rubber bush 33 located between two caulking portions 33b and 33c is brought into hermetical contact with the inside wall of the united covers 13 and 14 after the rubber bush 33 is deformed by the caulking operation, so that the sealing ability can be effected by an axially extending region between two caulking portions 33b and 33c. There is a tendency that deterioration (compressive permanent distortion) occurs at each of caulking portions 33b and 33c. Even if the sealing ability is reduced locally at these caulking portions 33b and 33c due to the above-described deterioration, the overall sealing ability of rubber bush 33 can be adequately maintained as long as rubber bush 33 is hermetically contacted with the inside wall of the united covers 13 and 14 in the axially extending region between two caulking portions 33b and 33c.

Other Embodiments

An essential part of the present invention resides in the above-described support and fixing structure realized by rubber bush 33. Therefore, sensor element 11 and other components can be modified flexibly. For example, the configuration of sensor element 11 can be formed into a platelike shape rather than being formed into a cup shape. In this case, electric heater 18 will be formed into a plate-like shape too, so that the electric heater can be laminated on this plate-like sensor element.

Furthermore, besides the concentration cell type sensor element 11 capable of generating an electromotive force corresponding to the difference of oxygen concentrations sensible by inside and outside electrodes 11a and 11b, the present invention can be applied to other air-fuel ratio sensors, such as a so-called limiting current type which applies a voltage between electrodes 11a and 11b of sensor element 11 and takes out an output current corresponding to an air-fuel ratio of exhaust gas.

Moreover, according to the above-described embodiments, covers 13 and 14 serving as housing members are caulked to generate a compressive stress applied to rubber bush 33. With this compressive stress, the lead wires 29, 30 and 31 can be firmly fixed with rubber bush 33. However, the present invention is not limited to the caulking structures disclosed in the above-described embodiments. For example, it is possible to sandwich rubber bush 33 between two covers 13 and 14 to give a compressive stress to rubber bush 33, so that the lead wires 29, 30 and 31 can be firmly fixed with rubber bush 33.

As this invention may be embodied in several forms without departing from the spirit of essential characteristics thereof, the present embodiments as described are therefore intended to be only illustrative and not restrictive, since the scope of the invention is defined by the appended claims rather than by the description preceding them, and all changes that fall within the metes and bounds of the claims, or equivalents of such metes and bounds, are therefore intended to be embraced by the claims.

What is claimed is:

1. An air-fuel ratio sensor comprising:

a sensor element for detecting an air-fuel ratio of gas fluid to be sensed;

housing means for holding and fixing said sensor element;

lead wires having one end connected to said sensor element, an intermediate portion extending inside said housing means and the other end taken out from an opening provided at an end portion of said housing means; and a rubber bush disposed inside said end portion of said housing means and having through holes into which said lead wires are inserted, wherein a compressive stress is applied to said rubber bush by said housing means to fix said lead wires hermetically with said rubber bush, and said rubber bush is made of a rubber material whose 100% modulus strength is equal to or larger than 60 Kgf/cm$^2$ even after said sensor is used under a temperature environment of 300° C. for 100 hours.

2. The air-fuel ratio sensor in accordance with claim 1, wherein said rubber bush is made of tetra phloro ethylene-par. phloro. ether group rubber.

3. The air-fuel ratio sensor in accordance with claim 1, wherein said end portion of said housing means is deformed at a caulking rate of 10 to 35% so as to applied said compression stress to said rubber bush.

4. The air-fuel ratio sensor in accordance with claim 1, wherein a multiple caulking structure comprising at least two caulking portions is provided on said end portion of said housing means.

5. An air-fuel ratio sensor comprising:

a cylindrical housing having an open end and a closed end;

a sensor element for detecting an air-fuel ratio of a sensed gas, said sensor element being accommodated in said housing at a predetermined position adjacent to said closed end of said housing;

at least one lead wire connected to said sensor element and extending beyond said open end of said housing;

a rubber bush provided at said open end of said housing so as to close said open end of said housing, said rubber bush having at least one through hole for holding said lead wire, wherein said rubber bush is compressed at a predetermined caulked portion where said housing is deformed radially inward, and said rubber bush is made of a rubber material whose 100% modulus strength is equal to or larger than 60 Kgf/cm$^2$ even after said sensor is used under a temperature environment of 300° C. for 100 hours, thereby preventing said rubber bush from causing a crack due to a tensile force acting in the vicinity of said caulking portion when said sensor is subjected to a high-temperature operating condition.

6. An air-fuel ratio sensor comprising:

a cylindrical housing having an open end and a closed end;

a sensor element for detecting an air-fuel ratio of a sensed gas, said sensor element being accommodated in said housing at a predetermined position adjacent to said closed end of said housing;

at least one lead wire connected to said sensor element and extending beyond said open end of said housing;

a rubber bush provided at said open end of said housing so as to close said open end of said housing, said rubber bush having at least one through hole for holding said lead wire, wherein said rubber bush is compressed at a predetermined caulked portion where a caulking force is applied to said housing, and a rubber material of said rubber bush is determined based on a tensile strength rather than a compressive strength, thereby preventing said rubber bush from causing a crack due to a tensile force acting in the vicinity of said caulked portion.

7. The air-fuel ratio sensor in accordance with claim 6, wherein said rubber material has a 100% modulus strength equal to or larger than 60 $Kgf/cm^2$ even after said sensor is used under a temperature environment of 300° C. for 100 hours.

* * * * *